US00PP23980P2

(12) United States Plant Patent
Bouwmeester

(10) Patent No.: US PP23,980 P2
(45) Date of Patent: Oct. 8, 2013

(54) *KNIPHOFIA* PLANT NAMED 'AMAZING FUN'

(50) Latin Name: *Kniphofia hybrida*
Varietal Denomination: Amazing Fun

(75) Inventor: Cor Bouwmeester, Noordwijkerhout (NL)

(73) Assignee: Compass Plants B.V., Hillegom (NL)

( * ) Notice: Subject to any disclaimer, the term of this patent is extended or adjusted under 35 U.S.C. 154(b) by 91 days.

(21) Appl. No.: 13/373,725

(22) Filed: Nov. 28, 2011

(51) Int. Cl.
*A01H 5/00* (2006.01)

(52) U.S. Cl.
USPC ..... Plt./443

(58) Field of Classification Search
USPC ..... Plt./443
See application file for complete search history.

*Primary Examiner* — June Hwu
(74) *Attorney, Agent, or Firm* — C. A. Whealy

(57) ABSTRACT

A new and distinct cultivar of *Kniphofia* plant named 'Amazing Fun', characterized by its upright growth habit; moderately vigorous growth habit; freely flowering habit; long flowering period; red-colored flower buds that develop into orange and yellow-colored flowers; and winter hardiness.

3 Drawing Sheets

Botanical designation: *Kniphofia hybrida.*
Cultivar denomination: 'AMAZING FUN'.

BACKGROUND OF THE INVENTION

The present invention relates to a new and distinct cultivar of *Kniphofia* plant, botanically known as *Kniphofia hybrida* and hereinafter referred to by the name 'Amazing Fun'.

The new *Kniphofia* originated from a cross-pollination conducted by the Inventor in 1998 of two unnamed proprietary seedling selections of *Kniphofia hybrida*, not patented. The new *Kniphofia* was discovered and selected by the Inventor as a single flowering plant from within the progeny of the stated cross-pollination grown in a controlled greenhouse environment in Noordwijkerhout, The Netherlands in 2000.

Asexual reproduction of the new *Kniphofia* plant by vegetative divisions in a controlled environment in Noordwijkerhout, The Netherlands since 2001 has shown that the unique features of this new *Kniphofia* plant are stable and reproduced true to type in successive generations.

SUMMARY OF THE INVENTION

Plants of the new *Kniphofia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Amazing Fun'. These characteristics in combination distinguish 'Amazing Fun' as a new and distinct *Kniphofia* plant:

1. Upright growth habit.
2. Moderately vigorous growth habit.
3. Freely flowering habit.
4. Long flowering period.
5. Red-colored flower buds that develop into orange and yellow-colored flowers.
6. Relatively more winter hardy than other *Kniphofia* plants.

Plants of the new *Kniphofia* can be compared to plants of the parent selections. Plants of the new *Kniphofia* differ from plants of the parent selections in the following characteristics:

1. Plants of the new *Kniphofia* are shorter than plants of the parent selections.
2. Plants of the new *Kniphofia* and the parent selections differ in flower color.
3. Plants of the new *Kniphofia* are more winter hardy than plants of the parent selections.

Plants of the new *Kniphofia* can also be compared to plants of *Kniphofia hybrida* 'Nancy's Red', not patented. In side-by-side comparisons conducted in Noordwijkerhout, The Netherlands, plants of the new *Kniphofia* differed from plants of 'Nancy's Red' in the following characteristics:

1. Plants of the new *Kniphofia* were shorter than plants of 'Nancy's Red'.
2. Plants of the new *Kniphofia* were more freely flowering than plants of 'Nancy's Red'.
3. Plants of the new *Kniphofia* and 'Nancy's Red' differed in flower color.

BRIEF DESCRIPTION OF THE PHOTOGRAPHS

The accompanying colored photographs illustrate the overall appearance of the new *Kniphofia* plant showing the colors as true as it is reasonably possible to obtain in colored reproductions of this type. Colors in the photographs may differ slightly from the color values cited in the detailed botanical description which accurately describe the colors of the new *Kniphofia* plant.

The photograph on the first sheet comprises a side perspective view of a typical plant of 'Amazing Fun' grown in a container.

The photograph on the second sheet is a close-up view of a typical inflorescence of 'Amazing Fun'.

The photograph on the third sheet is a close-up view of typical leaves of 'Amazing Fun'.

DETAILED BOTANICAL DESCRIPTION

The aforementioned photographs and following observations, measurements and values describe plants grown in containers during the late summer in an outdoor nursery in Noordwijkerhout, The Netherlands under cultural practices which approximate commercial production. During the production of the plants, day temperatures ranged from 14° C. to 28° C. and night temperatures ranged from 8° C. to 16° C. Plants were two years old when the photographs and description were taken. In the following description, color references are made to The Royal Horticultural Society Colour Chart, 2007 Edition, except where general terms of ordinary dictionary significance are used.

Botanical classification: *Kniphofia hybrida* 'Amazing Fun'.

Parentage:

*Female, or seed, parent.*—Unnamed proprietary seedling selection of *Kniphofia hybrida*, not patented.

*Male, or pollen, parent.*—Unnamed proprietary seedling selection of *Kniphofia hybrida*, not patented.

Propagation:

*Type.*—By vegetative divisions.

*Time to initiate roots.*—About three weeks at 20° C.

*Time to produce a rooted young plant.*—About 45 days at 20° C.

*Root description.*—Thick, fibrous, fleshy; creamy yellow in color.

*Rooting habit.*—Freely branching.

Plant description:

*Plant and growth habit.*—Herbaceous perennial; upright growth habit; basal rosette of leaves; flowering stems developing from the center of the basal rosette of leaves; moderately vigorous growth habit.

*Plant height, soil level to top of foliar plane.*—About 36 cm.

*Plant height, soil level to top of inflorescences.*—About 50.3 cm.

*Plant diameter.*—About 52 cm.

Foliage description:

*Arrangement.*—Alternate; simple; sessile.

*Length.*—About 37.5 cm.

*Width.*—About 8 mm.

*Shape.*—Lanceolate; strongly keeled.

*Apex.*—Long acuminate.

*Base.*—Broadly cuneate.

*Margin.*—Entire.

*Texture, upper and lower surfaces.*—Smooth, glabrous.

*Venation pattern.*—Parallel.

*Color.*—Developing leaves, upper surface: Close to 138A and 143B. Developing leaves, lower surface: Close to 138A. Fully expanded leaves, upper surface: Close to 143A to 143B; venation, close to 143A to 143B. Fully expanded leaves, lower surface: Close to 137B and 143A; venation, close to 137B and 143A.

Flower description:

*Flower arrangement and habit.*—Single funnelform flowers arranged on upright terminal racemes; freely flowering habit with about 100 flowers developing per inflorescence; flowers face outward to downward.

*Fragrance.*—None detected.

*Natural flowering season.*—Long flowering period, plants flower continuously from mid-summer to early autumn in The Netherlands.

*Flower longevity.*—Individual flowers last about five days on the plant; flowers not persistent.

*Inflorescence height.*—About 14 cm.

*Inflorescence diameter.*—About 4.2 cm.

*Flower diameter.*—About 9 mm.

*Flower depth (height).*—About 3.4 cm.

*Flower bud.*—Length: About 2.3 cm. Diameter: About 4.5 mm. Shape: Narrowly oblong. Color: Close to 41A to 41B; towards the base, close to 35B.

*Corolla.*—Arrangement: Six segments fused towards the base into a tube; 10% of segments are free. Segment length: About 2.5 cm. Segment width: About 2.5 mm. Lobe shape: Broadly ovate. Apex: Obtuse. Margin: Entire. Texture, upper and lower surfaces: Smooth, glabrous. Color: When opening, inner surface: Close to 11D; stripes near the apex, close to 22B to 22C. When opening, outer surface: Close to 29A; towards the base, close to 11D. Fully opened, inner surface: Close to 11D; color becoming closer to 14B with development. Fully opened, outer surface: Close to 14C; towards the base, close to 11D.

*Sepals.*—None observed.

*Peduncles.*—Length: About 47.1 cm. Diameter: About 5 mm. Strength: Strong. Aspect: Erect to about 5° from vertical. Texture: Smooth, glabrous. Color: Close to 144A and 144B.

*Pedicels.*—Length: About 2.5 mm. Diameter: About 1 mm. Strength: Strong. Aspect: About 90° from vertical. Texture: Smooth, glabrous. Color: Close to 144A.

*Reproductive organs.*—Stamens: Quantity: About six per flower. Filament length: About 2.8 cm. Filament color: Close to 11D. Anther shape: Oblong. Anther length: About 2 mm. Anther color: Close to 12A. Pollen amount: Moderate. Pollen color: Close to 8A to 8B. Pistils: Quantity: One per flower. Pistil length: About 2.5 cm. Style length: About 2.4 cm. Style color: Close to 154B to 154C. Stigma shape: Crested. Stigma color: Close to 22A. Ovary color: Close to 144B. Seeds and fruits: Seed and fruit development have not been observed on plants of the new *Kniphofia*.

Garden performance: Plants of the new *Kniphofia* have been observed to have good garden performance. Plants of the new *Kniphofia* have been observed to tolerate high temperatures of about 32° C. and to be winter hardy to USDA Hardiness Zone 7.

Pathogen & pest resistance: Plants of the new *Kniphofia* have not been observed to be resistant to pathogens and pests common to *Kniphofia*.

It is claimed:

1. A new and distinct *Kniphofia* plant named 'Amazing Fun' as illustrated and described.

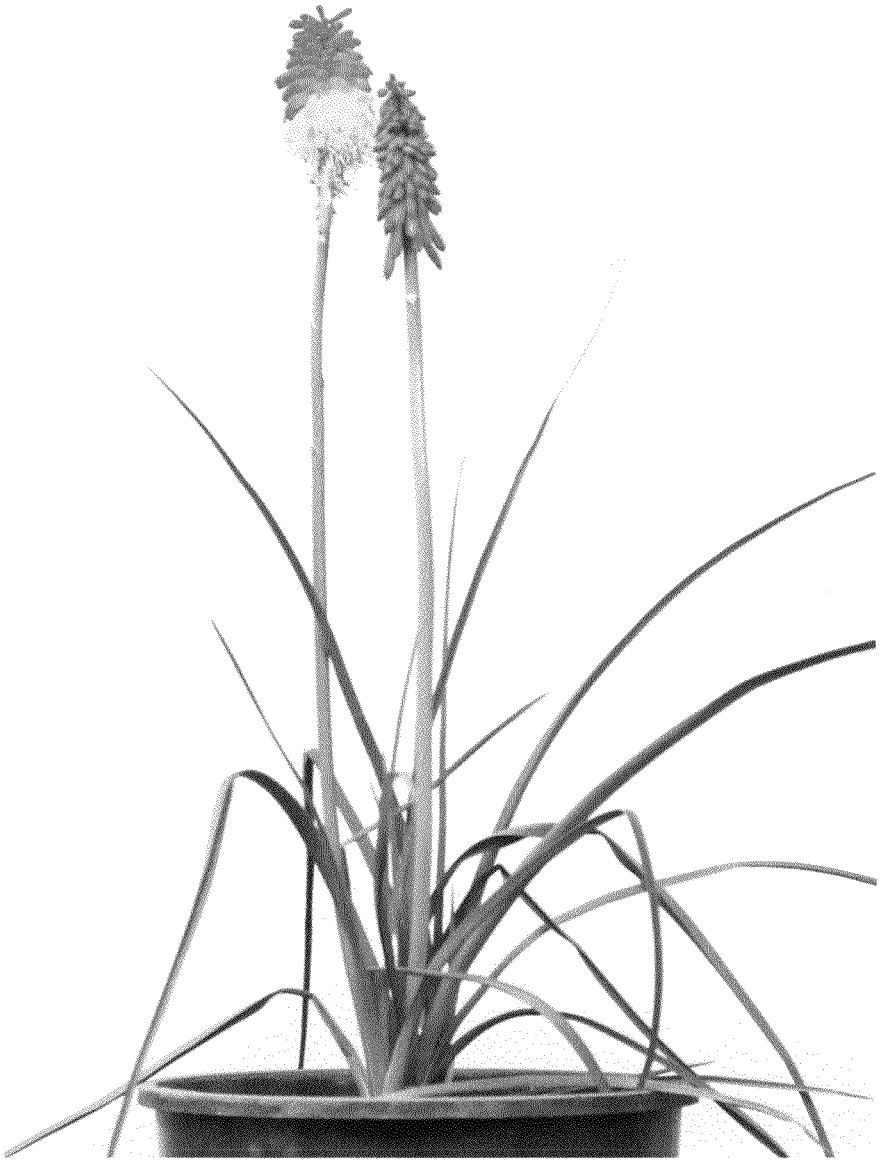

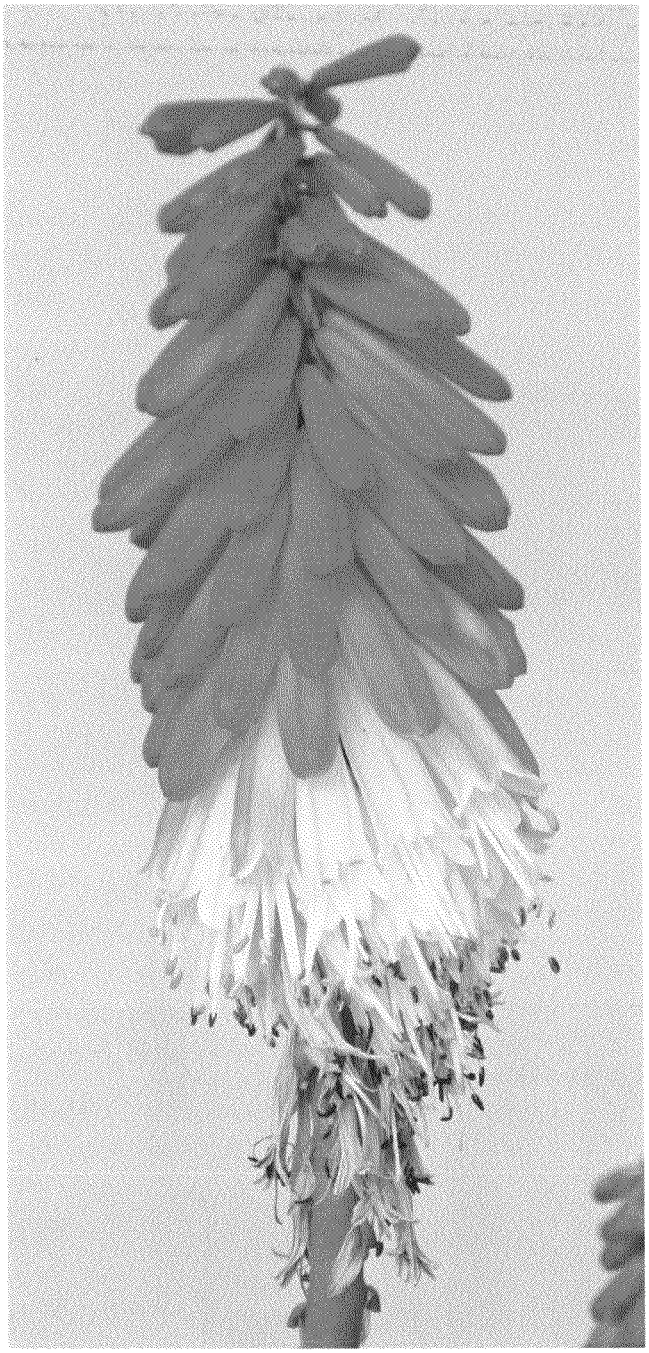

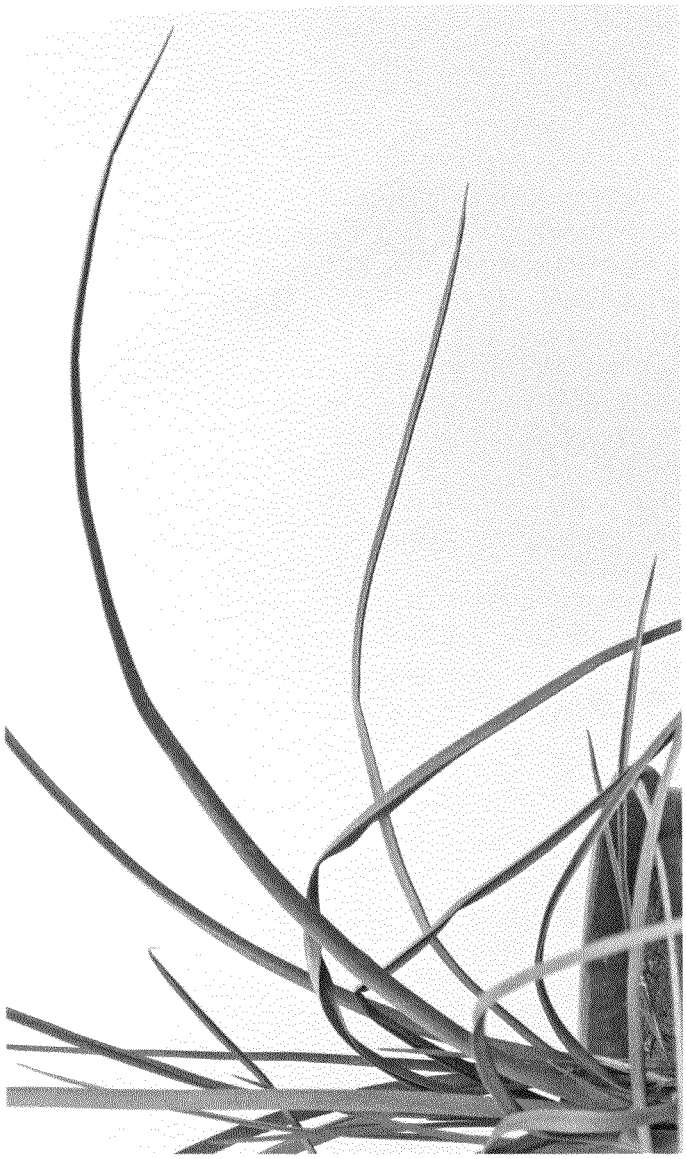

* * * * *